United States Patent [19]

Jamison et al.

[11] Patent Number: 5,062,844

[45] Date of Patent: Nov. 5, 1991

[54] METHOD AND APPARATUS FOR THE FIXATION OF BONE FRACTURES, LIMB LENGTHENING AND THE CORRECTION OF DEFORMITIES

[75] Inventors: Russell D. Jamison, Germantown, Tenn.; David Brumfield, Nesbit, Miss.; Richard Treharne, Memphis, Tenn.; Paul Wisnewski, Memphis, Tenn.; Robert Wigginton, Collierville, Tenn.; Michael Sherman, Memphis, Tenn.

[73] Assignee: Smith & Nephew Richards Inc., Memphis, Tenn.

[21] Appl. No.: 579,329

[22] Filed: Sep. 7, 1990

[51] Int. Cl.⁵ ............................................. A61F 5/04
[52] U.S. Cl. ...................................... 606/54; 606/56
[58] Field of Search .................................... 606/53-59

[56] References Cited

U.S. PATENT DOCUMENTS

| | | | |
|---|---|---|---|
| 2,055,024 | 9/1936 | Bittner, Jr. | 606/56 |
| 3,727,610 | 4/1973 | Riniker | 606/56 |
| 3,977,397 | 8/1976 | Kalnberz | 606/56 |
| 3,985,127 | 10/1976 | Volkov | 606/56 |
| 3,993,055 | 11/1976 | Volkov | 606/56 |
| 4,006,740 | 2/1977 | Volkov | 606/56 |
| 4,033,340 | 7/1977 | Kalnberz | 606/56 |
| 4,185,623 | 1/1980 | Volkov | 606/56 |
| 4,338,927 | 7/1982 | Volkov | 606/56 |
| 4,604,996 | 8/1986 | Nunamaker | 606/54 |
| 4,620,533 | 11/1986 | Mears | 606/54 |

*Primary Examiner*—Mickey Yu
*Assistant Examiner*—Michael Brown
*Attorney, Agent, or Firm*—Pravel, Gambrell, Hewitt, Kimball & Krieger

[57] ABSTRACT

A method and apparatus for the fixation of bone fractures, limb lengthening, and the correction of deformities uses an improved composite plastic carbon fiber ring that is formed in a mold, or machined with a stepped end portion that allows half rings to be assembled in a common plane. The method can use a mold wherein multiple rings can be formed by stacking the rings with a Teflon layer therebetween and wherein circumferential braid reinforcement of carbon fiber adds strength at the circumferential inner and outer curved surfaces of the rings and half rings.

25 Claims, 6 Drawing Sheets

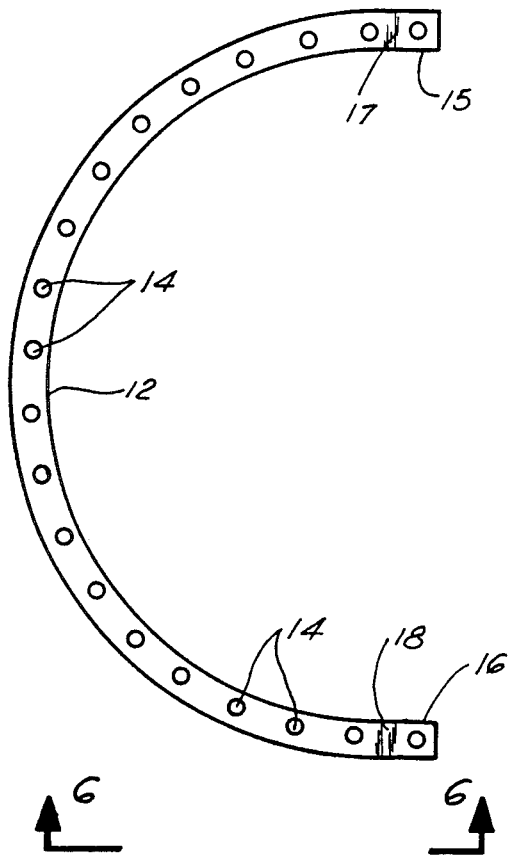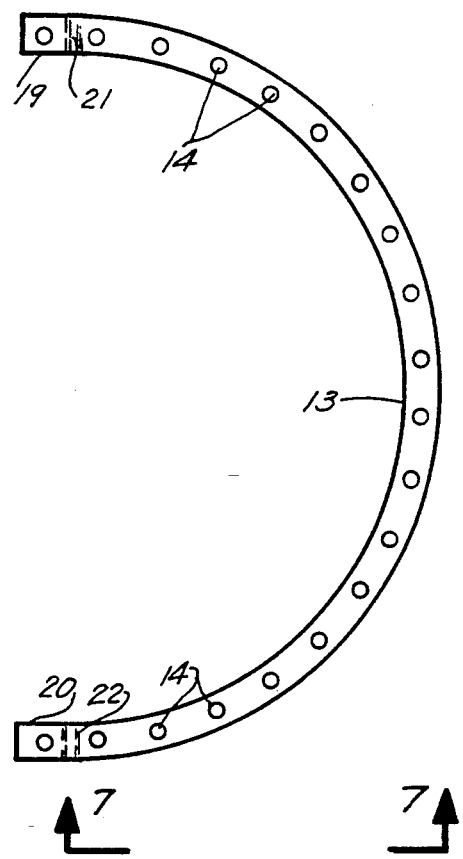
FIG. 4
FIG. 5
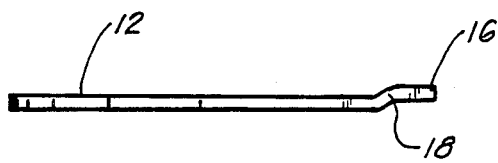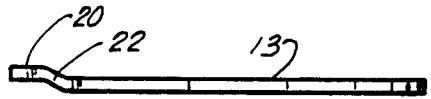
FIG. 6
FIG. 7

METHOD AND APPARATUS FOR THE FIXATION OF BONE FRACTURES, LIMB LENGTHENING AND THE CORRECTION OF DEFORMITIES

BACKGROUND OF THE INVENTION:

1. Field of the Invention

The present invention relates to external fixator systems useful in the repair of bone fractures, in limb lengthening, and in the correction of bone deformities. Even more particularly, the present invention relates to an improved external fixator system, useful with the so called "Ilizarov" method that uses rings held apart by threaded rods and threaded fasteners and wire rod components, used in the fixation of fractures, limb lengthening, and the correction of bone deformities wherein an improved ring construction that affords radiolucency is comprised of a composite plastic-carbon fiber material having lightweight, high strength, high modulus characteristics.

2. General Background

The repair of traumatized bone can be accomplished by the use of an external fixator device which includes a number of curved rings or curved half rings that are attached and spaced apart but structurally connected using a plurality of tie rods. These tie rods are simply inserted through one of several holes formed in each of the selected half rings or rings at a desired circumferential position and affixed thereto by bolting. Several rings and several tie rods can be used by the surgeon in order to create an overall frame about the patient's arm or leg. Transversely extending pins or wires attach to these rings and then extend transversely from the rings into the bones, so that the frame and transverse pins support and/or load the bone tissue in a desired manner.

This system is generally referred to in the art as the "Ilizarov" method and can be used for the purpose of external fixation of heavily damaged or heavily traumatized bone. The "Ilizarov" method can also be used for lengthening various congenital and acquired shortenings and other defects of skeletal segments wherein the rings and tie rods form part of compression-distraction apparatus.

The "Ilizarov" method is described generally in the Oct. 8, 1989 issue of Parade Magazine in an article entitled "Stretching The Body's Power To Grow", and in U.S. Pat. No. 4,615,338, issued to Gavril A. Ilizarov et al. The '338 Pat., entitled "Automatic Compression-Distraction Apparatus", is directed to an improved compression distraction apparatus. The '338 Ilizarov patent references earlier prior art publications of the same inventor, including USSR Inventor Certificate No. 848,011, cl.A 61 B 17/18, also published in the Bulletin of Inventions No. 27,1981. A second prior art disclosure relating to a drive of a compression distraction apparatus appears in USSR Inventor Certificate No. 865,284, cl.A 61 B 17/18, published in the Bulletin of Inventions No. 35,1981. These prior Ilizarov publications all relate generally to the Ilizarov external fixation system which uses metal rings, threaded rods, threaded fasteners, and other metallic components in the fixation of fractures, limb lengthening and the correction of bone deformities. Other attempts have been made to improve the "Ilizarov" method by modifying the ring and half-ring construction. A circular ring was developed by Kronner which used random carbon fiber reinforced nylon. This particular composite had a reported disadvantage of an inability to hold pins securely.

Fixano manufactured a device sold by Danek in the U.S. which used carbon fiber reinforced plastic half rings.

U.S. Pat. No. 3,977,397 discloses a liner impregnated phenolic ring of circular cross section.

Other patents relating to the Ilizarov system include the Koeneman et al. patents, U.S. Pat. Nos. 4,757,809 and 4,747,400. In the '400 Pat., the frame has side rails, each with a polyamide foam core, wrapped with a composite of graphite or glass fibers impregnated with thermo-plastic or thermo-setting resin.

European patent EP 87112273 and U.S. Pat. No. 4,604,996 issued to W. Herzberg discuss the use of glass fibre reinforced hoses and connections which can be filled with self-curing plastics, wherein such external fixture can be produced at low cost and offers no obstruction to x-rays.

The Mears patent, U.S. Pat. No. 4,620,533, relates to an apparatus for externally fixing bone fractures with clamps having universal ball joints to pins and a rigid bar. The bar is preferably of epoxy/carbon or epoxy/fiberglass composite, and the clamps are of nylon/carbon fiber composite, both being x-ray translucent.

The metallic nature of the Ilizarov system has presented clinical difficulties in the evaluation of patient's radiographs, because of the high radiopacity of the metallic parts. One of the most common problems incurred is that the surveillance of bone healing or bone distraction is impeded by radiographic shadowing resulting from the metallic components used in the Ilizarov system. Secondarily, the fully assembled Ilizarov frame can constitute a significant added weight which can be problematic in pediatric and upper extremity cases.

Prior attempts to solve this problem have not been able to supply the desirable physical and load carrying characteristics of the present invention including light weight, high strength, high modulus of elasticity (i.e., near that of steel) and radiolucency.

SUMMARY OF THE INVENTION

The present invention provides an improved method and apparatus for the fixation of bone fractures, limb lengthening, and the correction of deformities. The present invention provides improved radiolucency of the assembled Ilizarov components by using composite-material rings and half rings for use in conjunction with existing metallic tie rods, wires, pins, and compression-distraction components. An object of the present invention is to reduce the weight of the system in order to provide improved mobility which is important especially in pediatric cases. The desirable characteristics of the composite material half rings and rings of the present invention include light weight, high strength, high modulus of elasticity, and radiolucency.

The present invention thus provides an improved bone fixator apparatus for the fixation of fractures and the correction of congenital bone deformities, including a plurality of ring-like structures (both half rings and full rings) each having inner and outer annular curved surfaces, and spaced parallel flat upper and lower surfaces. Each ring is of a plastic-carbon composite material, the half rings being capable of assembly in pairs (e.g. using bolted connections) to define multiple rings and wherein offset end portions ensure that the two half rings in each pair are co-planar.

The carbon composite rings and half rings include carbon fiber oriented generally parallel to the plane of each ring. Preferably two circumferential carbon fiber reinforcement members or "braids" reinforce the inner and outer annular curved surfaces of each ring/half ring. A plurality of holes are spaced along the rings and reinforcement is positioned adjacent the holes for strengthening the half ring adjacent the holes.

A plurality of tie rod assemblies including rod members extend between half rings and through at least some of the holes in the half rings, and fasteners for securing each half ring to one or more of the tie rods is provided for maintaining spacing between the half rings during use. The end portions of each half ring are molded with the ring but out of the plane of the ring.

Each half ring and ring are preferably of a plastic, molded material of preferably carbon fiber reinforced epoxy.

In the method of the present invention, radiolucent rings and half rings can be formed for use in bone fixation for the fixation of fractures, limb lengthening, and the correction of bone deformities wherein tie rods and fasteners maintain spacing between two or more rings or half rings during use.

One embodiment of the method includes the laminating of a plurality of plates of carbon reinforced epoxy material and a machining of the laminated plates to form a final desired ring or half ring shape. The half rings and rings are then drilled with a plurality of circumferentially spaced holes in each ring, the holes adapting multiple rings for support.

The half rings can be formed with free end portions that include offsets or offset step portions that permit overlapping of two half rings at their respective offset step portions to form a single ring with a single ring plane, and further comprising the step of drilling a hole in each of the offset step portions.

As part of the method, a section modulus can be selected for the ring/half ring so that the ring is in fact stronger than a comparably shaped steel ring of the same or greater weight. Flexural rigidity is the product of modulus of elasticity and second moment of inertia. The flexural rigidity of the composite rings is preferably equal or substantially equal to that of steel rings presently in use. Since the composite rings have a modulus of elasticity typically only 30% that of steel, the moment of inertia needs to be greater in the composite rings for the flexural rigidity to be the same as that of a steel ring. The simplest way to achieve equal flexural rigidities is to increase the width and the thickness of the cross section of a composite ring which is equal in diameter to the steel ring. The flexural rigidity of the composite ring is thereby matched to the flexural rigidity of the metal ring in order that clinical experience with the metal ring can be carried over to the composite ring directly.

As an example, the modulus of elasticity of steel equals 28 million psi. The second moment of inertia for the presently available commercial steel rings equals about $3.6 \times 10^{-3}$ inches$^4$. The modulus of elasticity of the composite material of the present invention equals 8.8 million psi. The second moment of inertia for the rings and half rings of the present invention can be made to equal about $1.15 \times 10^{-3}$ inches$^4$. Therefore, the product of the modulus of elasticity and the second moment of inertia for both rings is equal to about $1.01 \times 10^5$ pounds-inch$^2$. That product of modulus of elasticity and second moment of inertia is the flexural rigidity of the ring. With the present invention, the preferred value for the flexural rigidity is about $2.0 \times 10^4$ to $5.0 \times 10^5$ pounds-inch$^2$.

In another embodiment of the method, radiolucent rings and half rings are formed by molding (e.g. compression molding) a ring body of a composite of plastic and graphite fibers into a desired ring or half ring shape with a mold having a cavity wherein a sufficient number of graphite fibers (preferably in the form of circumferentially extending "braids") are oriented parallel to the plane of the ring/half ring in order to produce a flexural rigidity that at least approaches the flexural rigidity of steel rings of the same diameter. As an optional step, the method can use a plurality of cylindrical posts disposed within the mold cavity to define a plurality of circumferentially spaced openings in the ring upon completion of molding.

The mold is preferably in the form of a ring-like shape having innermost and outermost respective circumferential edge portions, and graphite reinforcement braids are placed respectively on opposite sides of a circumferential line that intersects the plurality of posts so that the graphite reinforcement braids respectively track the innermost and outermost respective circumferential edge portions of the ring upon completion of the molding process.

The holes in the rings can be reinforced with polymer sleeves which are placed over each of the posts prior to the molding step.

Multiple rings can be manufactured in molds which are nested one inside the other. Multiple rings can be manufactured simultaneously by stacking rings between adjacent layers of polytetrafluoroethylene (PTFE), for example, prior to compression molding.

BRIEF DESCRIPTION OF THE DRAWINGS:

For a further understanding of the nature and objects of the present invention, reference should be had to the following detailed description, taken in conjunction with the accompanying drawings, in which like parts are given like reference numerals, and wherein:

FIG. 4 is a top view of the preferred embodiment of the apparatus of the present invention illustrating a half ring element;

FIG. 5 is another top view of a second half ring element;

FIG. 6 is a side view taken in the direction indicated by lines 6—6 of FIG. 4;

FIG. 7 is a side view taken in the direction indicated by lines 7—7 of FIG. 4;

Figure 1:
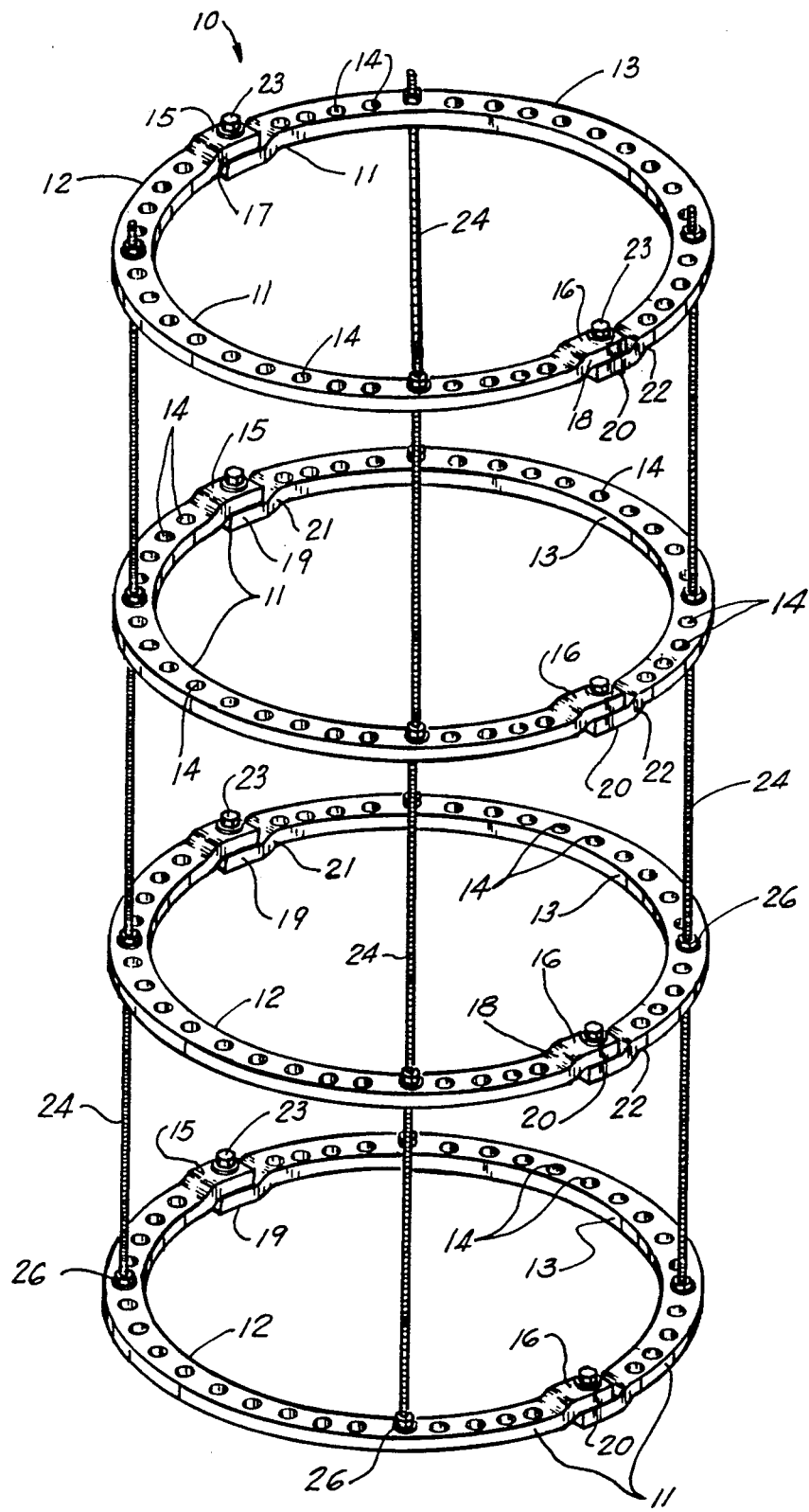
FIG. 1 is a perspective view of the preferred embodiment of the apparatus of the present invention.
Figure 2:
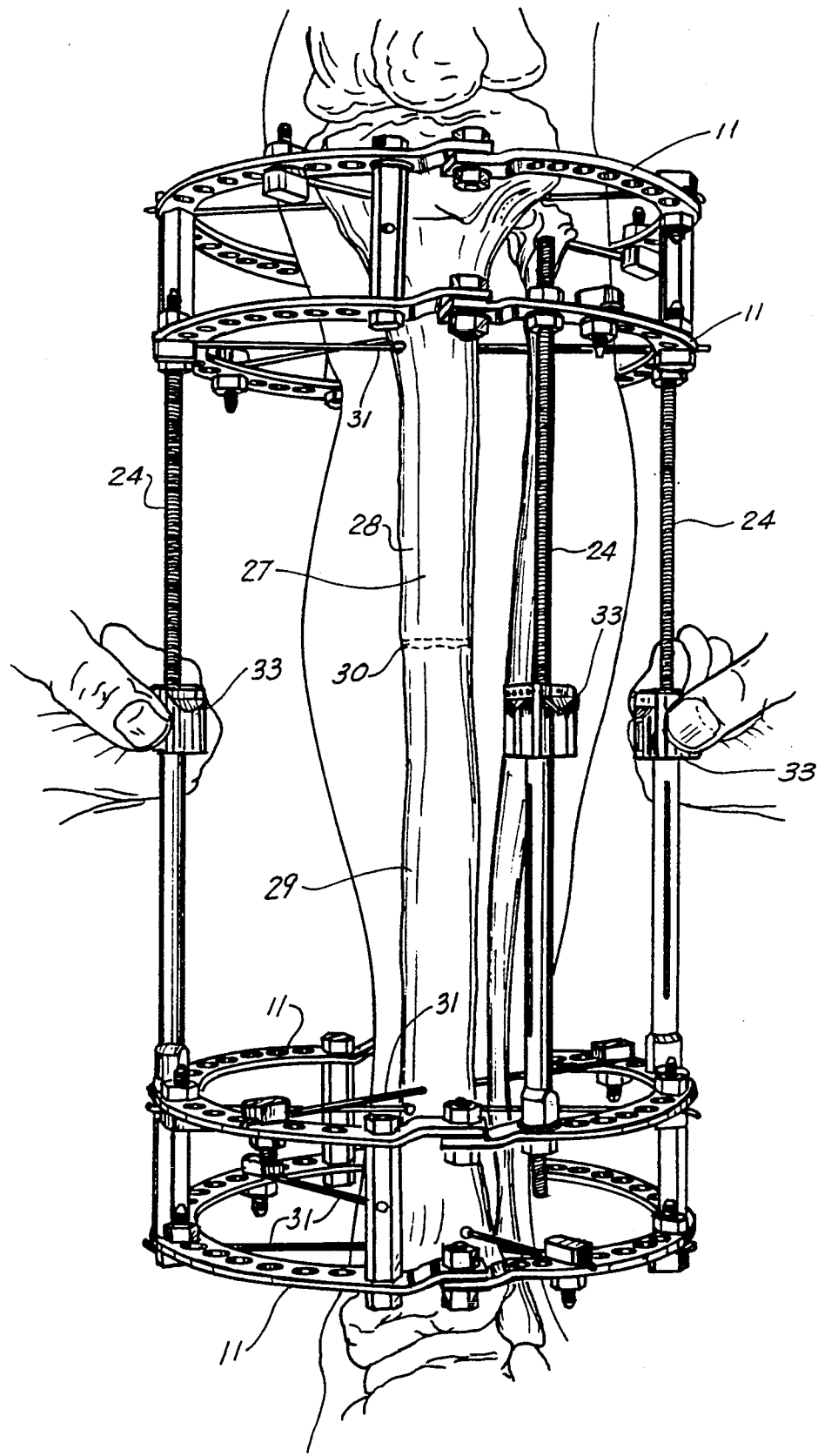
FIG. 2 is a fragmentary perspective view of the preferred embodiment of the apparatus of the present invention shown in operative position.
Figure 3:
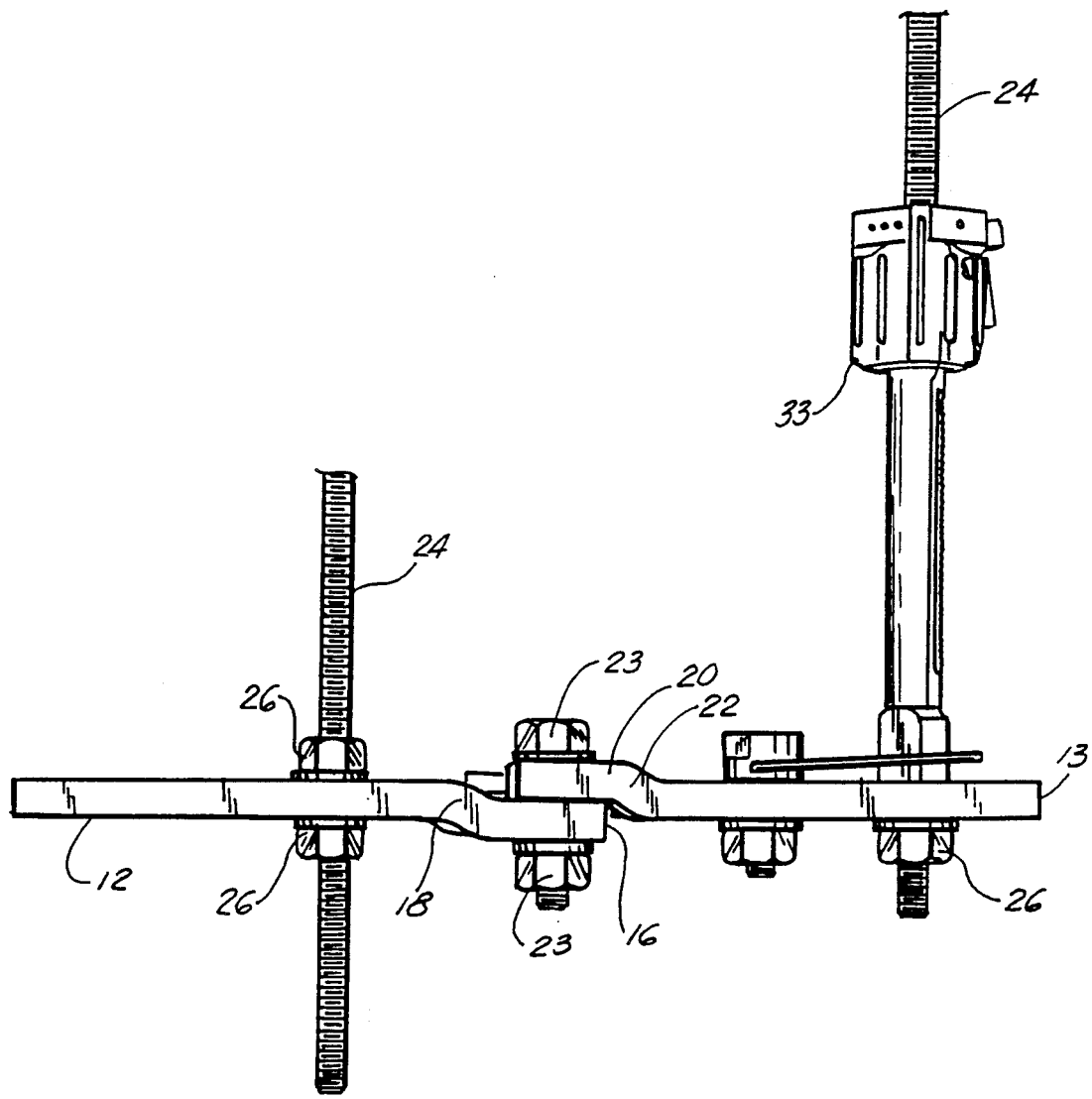
FIG. 3 is a fragmentary perspective view of the preferred embodiment of the apparatus of the present invention illustrating use with a compression-distraction device.

DETAILED DESCRIPTION OF THE PREFERRED EMBODIMENT:

FIGS. 1-3 show generally the preferred embodiment of the apparatus of the present invention designated generally by the numeral 10. Bone fixator apparatus 10 is useful in the fixation of fractures, limb lengthening, and correction of bone deformities. The apparatus includes a plurality of half rings 12, 13 that can be connected end-to-end to form full rings 11. Each half ring 12, 13 and each ring 11 includes a plurality of spaced openings 14 for the attachment of tie rods 24 therethrough.

Each half ring 12, 13 includes end portions 15, 16 and 19, 20 respectively. The end portions 15, 16 and 19, 20 are provided with offset steps 17, 18 and 21, 22 respectively so that a pair of half rings 12, 13 can be connected together such as by bolting, for example, using bolted connections 23.

The plurality of openings 14 in each half ring 12, 13 and through each ring allow tie rods 24 to be inserted therethrough. Nuts 26 are placed on each tie rod 24, respectively above and below each ring 11 and/or half ring 12, 13, as shown in FIGS. 1 and 2 for the purpose of spacing the rings 11 and half rings 12, 13 apart. Thus, the rings 11, half rings 12, 13, and tie rods 24 as well as the bolted connections 23 and nuts 26 form an overall frame as shown in FIG. 1 that can be placed around a bone to be repaired after trauma or to be lengthened because of, for example, congenital deformity.

In FIG. 2, bone 27 is shown in an operative position with respect to the plurality of rings 11 and tie rods 24. Bone 27 includes upper segment 28 and lower segment 29 with fracture 30 being schematically illustrated. A plurality of transversely extending wires or pins 31 can be mounted securely to rings 11 and half rings 12, 13. This overall apparatus of rings, tie rods, bolted connections and wires/pins has typically been manufactured of metallic construction, such as steel or metallic alloy in the prior art. FIG. 2 also shows tightening means 33.

In accordance with the present invention, rings 11 are assembled with two half rings 12, 13, each manufactured of a radiolucent construction of preferably plastic-carbon composite, such as epoxy/carbon-fiber composite. In accordance with the method and apparatus of the present invention, the plastic-carbon composite half rings include one or more carbon fiber braid members 45, 46 oriented generally parallel to the plane of the ring (See FIGS. 10 and 11). A plurality of holes 14 are spaced along the rings 11 and half rings 12, 13 and circumferential reinforcement (fibers 47—see FIGS. 10 and 11) is positioned adjacent the holes for strengthening the half ring adjacent the holes. A plurality of tie rods 24 and tie rod nuts 26 are used to affix the half rings and rings through the holes 14 in the half rings and rings for maintaining spacing between half rings 12, 13 and rings 11 during use.

Figure 8:
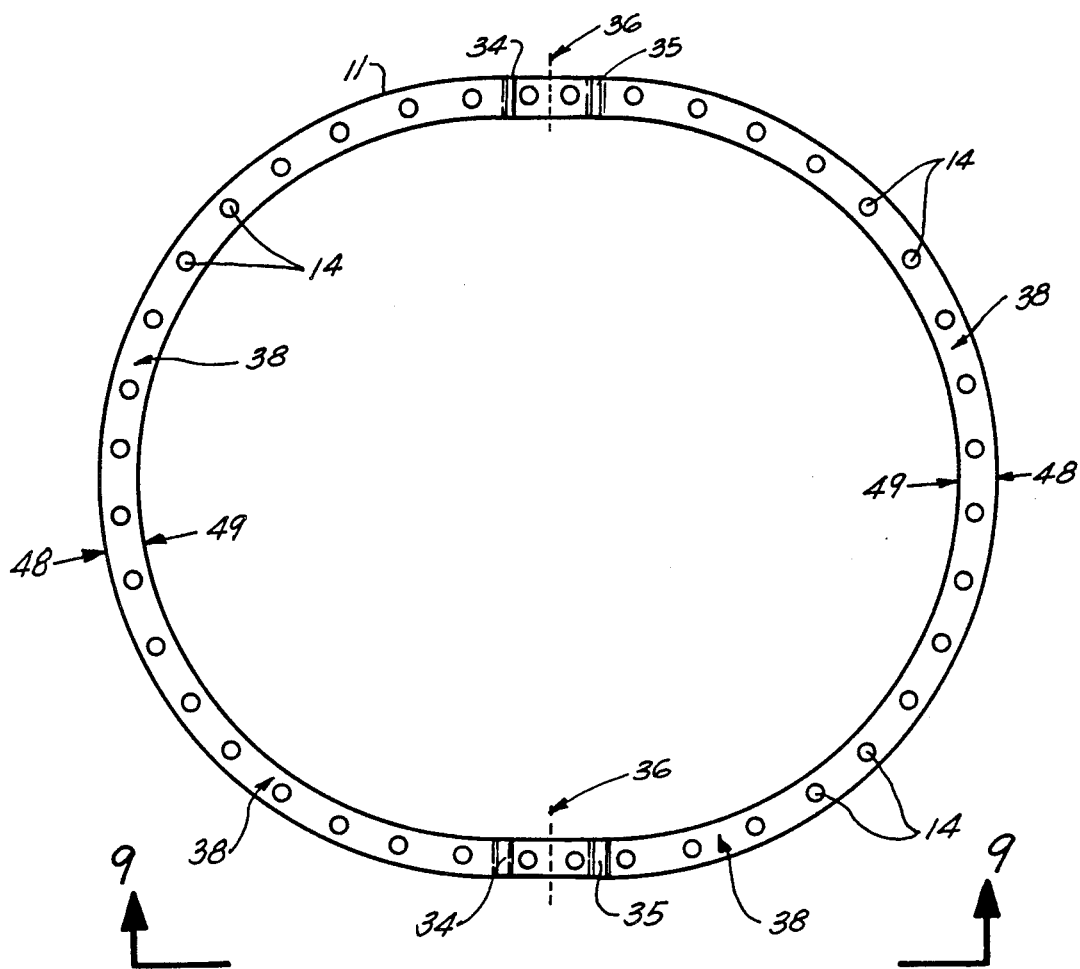
FIG. 8 is a top view of the preferred embodiment of the apparatus of the present invention illustrating a full ring.
Figure 9:
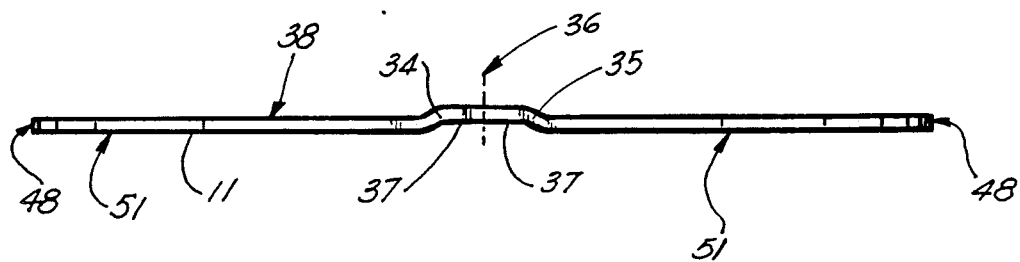
FIG. 9 is a side view taken in the direction indicated by lines 9—9 of FIG. 8.
Figure 10:
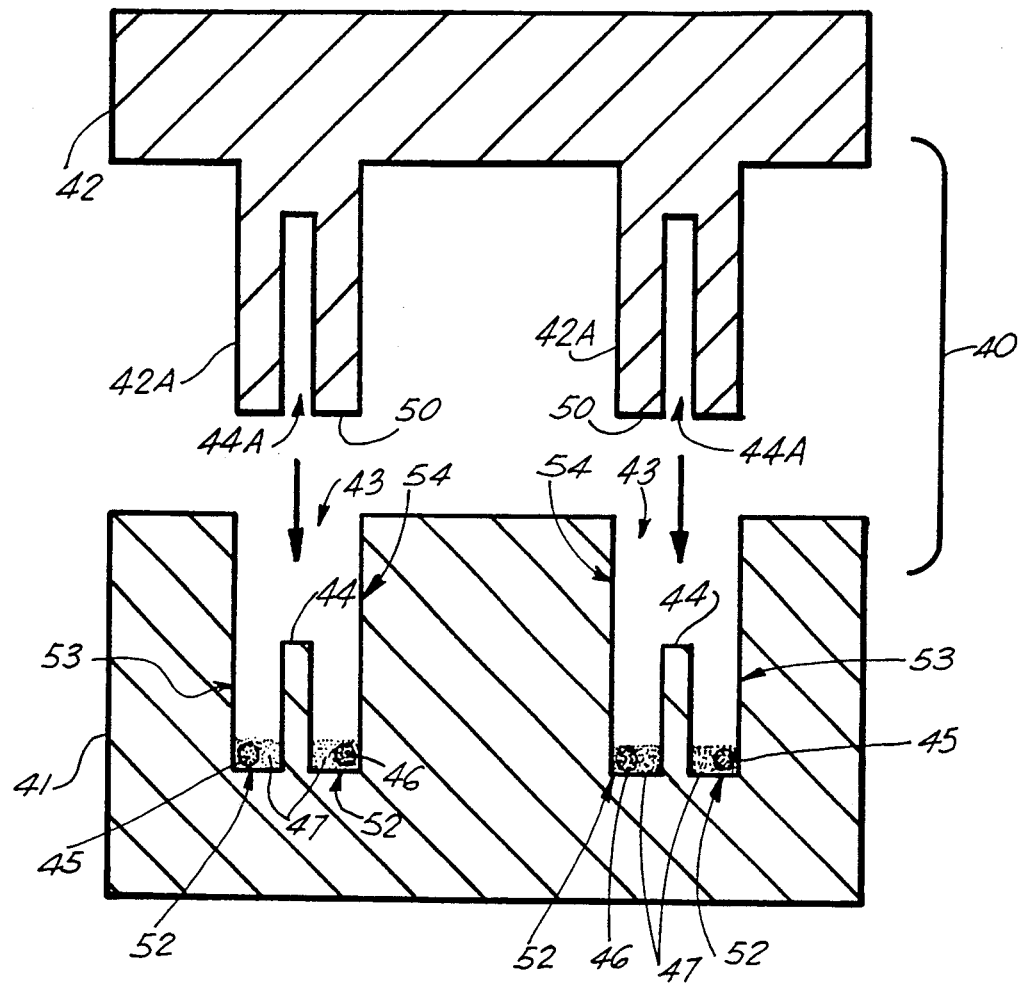
FIG. 10 is sectional elevational view illustrating the method of the present invention using compression moldings and prior to the mold step.
Figure 11:
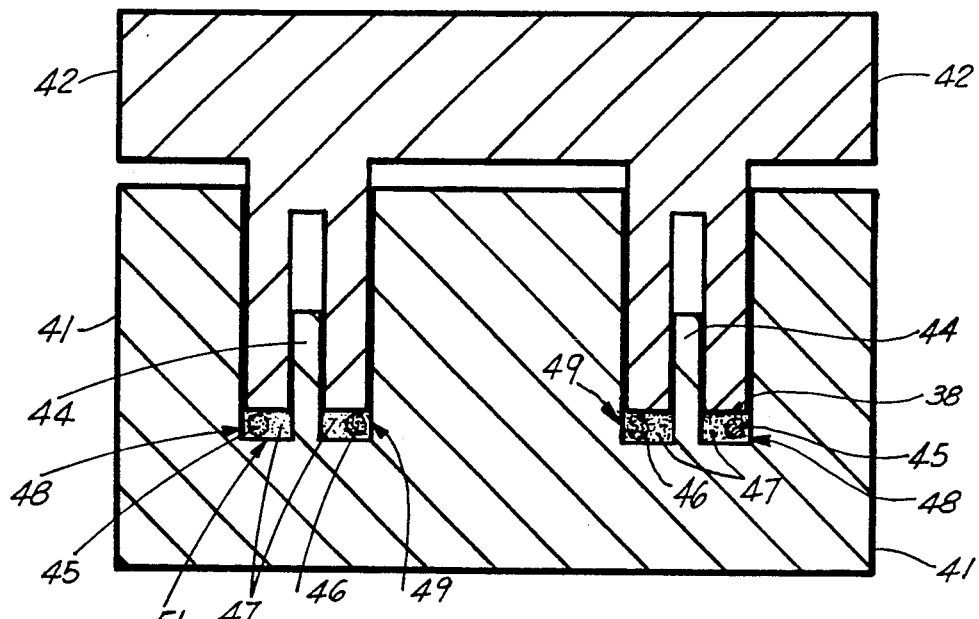
FIG. 11 is a sectional elevational view illustrating the method of the present invention during compression molding.

FIGS. 4-7 illustrate the half rings 12, 13 in plan view (FIGS. 4 and 5) and in side view (FIGS. 6 and 7). The half rings 12, 13 can be molded in such a half ring shape, or can be molded as a full ring structure 11 as shown in FIGS. 8 and 9 so that the half rings 12, 13 could be formed by cutting the full ring 11 along the dotted line 36 of FIGS. 8 and 9 so that a single ring could be manufactured in a mold (see FIGS. 10 and 11) and then cut to form the half rings. Thus, the molded ring 11 would have a stepped portion defined by steps 34, 35 with the offset portions providing an undersurface 37 which is at the same horizontal elevation as the upper surface 38 of the ring 11. In this manner, when the rings are assembled as shown in FIGS. 1 and 2, the plane of the ring 11 will be a single plane (i.e., the two half-rings will be co-planar) because the upper surface of each half ring and the lower surface of each half ring are at the same elevation. In FIGS. 10 and 11, the preferred method of the present invention is illustrated for forming a ring 11 of plastic/carbon-fiber composite using compression molding.

In FIG. 10, mold 40 is shown as comprising a lower die member 41 and an upper die member 42. A cavity 43 includes a plurality of post members 44 which produce the openings 14 of the molded ring 11. Upper die 42 includes a lowermost projecting portion 42A having a plurality of sockets 44A that receives slidably the plurality of posts 44. As many posts 44 will be provided as holes 14 are desired in the final molded ring 11.

A plurality of preferably two carbon graphite braids 45, 46 are placed within the mold cavity 43, and on opposite sides of the plurality of posts 44. There is an outermost circumferentially extending carbon graphite braid member 45 that tracks the outermost curved peripheral surface 48 of the ring as shown in FIGS. 10 and There is also preferably an innermost circumferentially extending carbon graphite braid member 46 which tracks inner curved surface 49. Adjacent posts 44 and openings 14, random carbon graphite fibers 47 are placed when the ring is molded. The molded article thus comprises a plastic (preferably epoxy) with inner and outer carbon graphite braids 46, 45 placed circumferentially at the innermost and outermost respective curved surfaces 49, 48 of ring 11, and with random graphite fibers 47 placed adjacent posts 44 and thus openings 14 after molding is completed.

The lowermost surface 50 of lower projection 42A of upper die 42 defines an uppermost surface 38 of ring 11 as finally molded. The bottom 52 of mold cavity 43 defines the lowermost surface 51 of ring 11 upon molding. Mold cavity 43 has a vertically extending curved side wall 53 which defines the configuration of outermost circumferential curved surface 48 of ring 11. Generally vertical curved surface 54 of die member 41 defines the innermost curved circumferential surface 49 of ring 11. The rings 11 and half rings 12, 13 preferably have a flexural stiffness of between $2.0 \times 10^4$ to $5.0 \times 10^5$ pounds-inch$^2$.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A bone fixator apparatus for fixation of fractures, limb lengthening, and the correction of bone deformities comprising:
   (a) a plurality of half rings, each having inner and outer annular curved surfaces, and spaced parallel, flat upper and lower surfaces, each half ring being made of a plastic-carbon composite material, the half rings being selectively connectable to form pairs that define multiple rings upon assembly such as by bolting, each ring defining a plane;

(b) the plastic-carbon composite half rings including one or more carbon fiber braid members oriented generally parallel to the plane of the half ring;

(c) a plurality of holes spaced along the half rings;

(d) circumferential reinforcement means positioned adjacent the holes for strengthening the half ring adjacent the holes; and (e) a plurality of tie rods assemblies including rod members extending during use between half rings and through at least some of the holes in the half rings, and fasteners for securing each half ring to one or more tie rods, for maintaining spacing between the half rings during use.

2. The apparatus of claim 1 wherein the end portions of each half ring are molded with the ring, but out of the plane of the ring.

3. The apparatus of claim 1 wherein the half ring is of a molded material.

4. The apparatus of claim 2 or 3 wherein the rings are carbon fiber reinforced epoxy.

5. A bone fixator apparatus for fixation of fractures, limb lengthening, and the correction of bone deformities, comprising:

(a) a plurality of generally circular rings, each having inner and outer curved surfaces, and generally flat, parallel space upper and lower surfaces;

(b) a plurality of circumferentially spaced openings in each ring extending between the upper and lower flat surfaces;

(c) at least one of the rings being of a composite plastic-carbon fiber material;

(d) a plurality of tie rod assemblies including rod members extending between the rings and through at least some of the holes in the rings and fasteners removably affixable to the rods for maintaining spacing between the rings during use; and (e) circumferential reinforcement means for reinforcing the rings along at least one of its curved surfaces comprising carbon fibers oriented in the plane of the ring at one of the curved surfaces.

6. The apparatus of claim 5 wherein the circumferentially spaced openings are reinforced with random carbon fiber placement adjacent the holes.

7. The apparatus of claim 5 wherein the plastic-carbon fiber composite ring has a flexural rigidity of between about $2.0 \times 10^4$ and $5.0 \times 10^5$ pounds-inch$^2$.

8. The apparatus of claim 5 wherein the plastic-carbon fiber composite ring is carbon fiber reinforced epoxy.

9. The apparatus of claim 5 wherein the ring is machined from laminated plates of carbon reinforced epoxy.

10. The apparatus of claim 5 wherein the rings are of a molded carbon fiber reinforced epoxy.

11. A method of forming radiolucent rings and half rings for use in bone fixation for the fixture of fractures, limb lengthening, and the correction of bone deformities wherein tie rods and fasteners maintain spacing between two or more half rings or rings during use, comprising the steps of:

(a) laminating a plurality of plates of carbon reinforced epoxy material;

(b) machining the laminated plates to a final desired ring or half ring shape; and (c) drilling a plurality of circumferentially spaced holes in each ring.

12. The method of claim 11 wherein in step "b", the final shape is a half ring, and the half ring is formed with two free end portions, each with an offset step portion that permits overlapping of two half rings at their respective offset step portions to form a single ring with a single ring plane, and further comprising the step of drilling a hole in each offset step portion.

13. The method of claim 11 wherein the laminated plates have carbon fibers oriented at various angles with quasi-isotropic elastic properties.

14. The method of claim 11 wherein the modulus of elasticity is about nine million p.s.i.

15. A method of forming radiolucent rings and half rings for use in bone fixation for the fixture of fractures, limb lengthening, and the correction of bone deformities wherein tie rods and fasteners maintain spacing between two or more rings during use, comprising the steps of:

(a) molding a ring body of a composite of plastic and graphite fibers into a desired ring or half ring shape with a mold having a cavity wherein a sufficient number of graphite fibers are oriented in the plane of the ring to produce a flexural rigidity of at least $2.0 \times 10^4$ pounds-inch$^2$.

16. A method of forming radiolucent rings and half rings lengthening, and the correction of bone deformities wherein tie rods and fasteners maintain spacing between two or more rings during use, comprising the steps of:

(a) a mold defining the desired ring or half-ring shape is provided and a graphite fiber reinforcement braid is placed in the mold and circumferentially about the mold; and (b) using a plurality of cylindrical posts within the mold cavity to define a plurality of circumferentially spaced openings in the ring.

17. The method of claim 16 wherein there are two graphite reinforcement braids placed respectively on opposite sides of a circumferential line that intersects the plurality of posts.

18. The method of claim 17 wherein the mold is ring-like in shape, having innermost and an outermost respective circumferential edge portions and the graphite reinforcement braids are positioned respectively at the innermost circumferential edge of the mold and at the outermost circumferential edge of the mold.

19. The method of claim 16 further comprising the step of placing random carbon fiber material generally between the two graphite reinforcement braids.

20. The method of claim 15 or 16 further comprising the step of selecting a section modulus for the ring so that the ring is stronger than a comparably shaped steel ring of the same or greater weight.

21. The method of claim 15 or 16 further comprising the steps of reinforcing the holds by placing sleeves over each of the posts prior to molding, and molding the sleeves to the ring element as part of the ring element.

22. The method of claim 21 wherein the sleeves are of a polymer material.

23. The method of claim 15 or 16 wherein in step "a" multiple rings are formed in the mold by placing spacer layers between adjacent, stacked rings.

24. The method of claim 21 wherein some of the rings are of different sizes.

25. The method of claim 15 or 16 wherein a full ring is formed that can be divided into two half rings.

* * * * *